United States Patent
Spinello

[19]

[11] Patent Number: 6,113,574
[45] Date of Patent: Sep. 5, 2000

[54] ANESTHETIC INJECTION APPARATUS AND METHODS

[76] Inventor: Ronald P. Spinello, 4169 Sycamore La., Red Lion, Pa. 17356

[21] Appl. No.: 09/122,915

[22] Filed: Jul. 27, 1998

[51] Int. Cl.[7] .................................................. A61M 5/145
[52] U.S. Cl. ................................. 604/131; 128/DIG. 12; 604/154
[58] Field of Search ................................ 604/154, 131, 604/65; 128/DIG. 12, DIG. 3

[56] References Cited

U.S. PATENT DOCUMENTS

| | | | |
|---|---|---|---|
| 4,151,845 | 5/1979 | Clemens | 128/DIG. 13 |
| 4,747,824 | 5/1988 | Spinello . | |
| 5,000,739 | 3/1991 | Kulisz | 128/DIG. 12 |
| 5,180,371 | 1/1993 | Spinello . | |
| 5,256,157 | 10/1993 | Samiotes et al. | 128/DIG. 13 |
| 5,295,967 | 3/1994 | Rondelet | 128/DIG. 12 |
| 5,389,071 | 2/1995 | Kawahara et al. | 128/DIG. 12 |
| 5,389,078 | 2/1995 | Zalesky et al. | 128/DIG. 13 |
| 5,464,391 | 11/1995 | DeVale | 128/DIG. 13 |
| 5,662,611 | 9/1997 | Beiser et al. | 128/DIG. 13 |

*Primary Examiner*—Paul J. Hirsch
*Attorney, Agent, or Firm*—Galgano & Burke

[57] ABSTRACT

Apparatus and methods for the power and computer assisted injection of local anesthetic into a patient in a virtually pain free manner, in which anesthetic pressure is automatically monitored as an input to the computer, in which the patient is able at any time to order the automatic reduction of anesthetic pressure and in which a simple single pole switch is the only control input to the computer required of the doctor administering the injection.

14 Claims, 5 Drawing Sheets

ANESTHETIC INJECTION APPARATUS AND METHODS

FIELD OF THE INVENTION

The invention relates to the injection of local anesthetic into a body part, particularly the mouth, by means of hollow hypodermic needles.

BACKGROUND PRIOR ART

Local anesthetics injected into the body by hand-held syringes to enable otherwise painful medical procedures to be performed without pain have been used for over 100 years. The lesser but nevertheless real pain caused by the syringes persisted until 1986 when the applicant invented an apparatus and method to eliminate it. Such are disclosed in the applicant's U.S. Pat. Nos. 4,747,824 and 5,180,371, which are incorporated herein by reference for their showing of the prior art as it exists today.

The applicant's prior invention provides a computer controlled power driven pump for feeding anesthetic through the needle at, selectively, either one of two different, pre-programmed rates of flow. The lower flow rate is empirically determined to be at or below the maximum rate at which, for the average patient, the anesthetic is absorbed into most tissue without pain. The low flow rate is started at the time of implanting the needle and is continued for a period of time which the doctor estimates to be necessary to pre-numb the surrounding tissues sufficiently to receive the high flow rate without pain.

The high flow rate then drives the anesthetic to the desired nerve target within a reasonable time. The total time may or may not be greater than that taken by the conventional hand syringe injection but the trade off is freedom from pain and a much more pleasant procedure for the doctor and patient alike.

The injection, however, of local anesthetic by any of the prior art methods and apparatus presents a dilemma to the doctor. Whereas a low flow rate for anesthetic is painless, the time the syringe, in the hand of the doctor, remains with the needle implanted in the patient can be a tiring ordeal for the patient and doctor alike, even if the ultimate objective of complete numbing is achieved. Also, a slow rate of injection can defeat the ultimate objective of effective numbing of a body part and can saturate soft tissues to the extent of injury before the nerve is anesthetized. On the other hand, more rapid injection rates translate into higher pressure which instantly translates into pain for the patient. These facts, coupled with the fact that different patients have differing thresholds of pain, and the fact that even the same patient can have differing sensitivity in different injection sites, spell trouble for the doctor. Optimizing the numbing procedure without pain is virtually impossible using all of the known prior art techniques.

Accordingly, the present invention abandons the applicant's basic prior art concept of providing the doctor with a selection of two different, pre-determined flow rates, high and low, which are chosen by a double acting selector switch on a somewhat arbitrary time schedule. First, the double pole selector switch concept is not user friendly for the doctor because it introduces the possibility of human error. Just as important, the prior art introduces a subjective decision by the doctor as to when he dares to select the high flow rate. He faces the dilemma of pain for the patient versus wasted time, poor numbing results, and tissue damage.

An object of the present invention, therefore, is to provide for the injection of local anesthetic in a user friendly manner, in less time and often in lesser amounts to achieve the same degree of numbing, all without discomfort for the patient.

Another object of the invention is to provide apparatus and method which achieve a consistently effective intraligamentary or "PDL" injection of local anesthetic in dentistry which is substantially free of pain and tissue damage for the patient and which, for the benefit of the doctor and patient alike, can often be accomplished in much less time using less anesthetic and with a very low failure rate.

Another object of the invention is to provide an apparatus and method for the painless injection of local anesthetic in which, at any time in the procedure, the patient can arrest the rate of flow of the anesthetic and instantly reduce the pressure of the anesthetic in the tissues and, therefore, preclude pain.

Another object of the invention is to provide an apparatus and method for the painless injection of local anesthetic in which the pressure of the anesthetic at the needle tip within the patient is measured and utilized in the injection process.

Another object of the invention is to provide an improved disposable needle assembly for conveying the anesthetic from the reservoir into the tissue.

BRIEF DESCRIPTION OF THE INVENTION

The present invention, rather than providing two alternatively selectable uniform flow rates for the liquid anesthetic from the computer-controlled, power driven pump system, provides one increasing rate of flow on a predetermined curve which can be stopped and restarted at any time. Thus, only one selection is required by the doctor and this can be done by means of one single-pole (on/off) switch. The ever increasing flow rate is a simple curve, preferably running the full range from zero to the maximum clinically approved rate at which anesthetic should be infused into human tissues. The curve need not necessarily be linear but can provide for progressively larger increases as a function of time as the procedure advances i.e., the flow rate curve steepens. In the best of all worlds, the injection, tracking the curve, will achieve complete numbing quickly and virtually without pain. The doctor will end the procedure whenever the indicated dosage for that particular procedure, for example, from 0.4 to 1.7 ml of liquid, has been injected.

The invention also recognizes the absolute relationship between pain felt by the patient and liquid pressure at the lumen of the needle implanted in the patient's tissues. If, the patient at any time during the injection feels discomfort, which is the precursor of actual pain, he or she is provided with means to instantly reduce the pressure by arresting the flow and, therefore, avoid the pain by signaling the pump via a simple hand-held switch. The delivery system automatically drops the pressure and either automatically or on command begins to re-build the pressure on the same ever increasing flow rate curve. The second pass on the flow rate curve is free of pain for almost all of the more sensitive patients, although the patient may arrest the flow and re-start it as often as necessary.

If the patient does not intervene to lower the pressure on any pass up the curve but if the pressure nevertheless builds to the maximum pressure, the instrument will automatically sense the pressure and itself command the reduction of pressure in the same manner as the patient. Thus, the patient and the instrument are protected while the anesthetic is administered virtually without pain and in most cases close to the minimum theoretical time possible to achieve effective and painless anesthesia for any given patient.

The method and apparatus lend themselves particularly to the performance in dentistry of the intraligamentary or PDL injection in which the needle is seated in the sulcus to seal tightly in the narrow ligament which separates the tooth from the bone. Flow of anesthesia is begun on the flow rate curve, and continues automatically upward to develop the pressure necessary to drive the liquid through the ligament space to the nerve bundle at the bottom of the root. In accordance with the invention, if the seal between the needle tip and the ligament is tight, the pressure may build quickly even at relatively slow rates of flow to the maximum permissible pressure and the instrument will promptly signal this fact to the doctor by sensing high pressure. As the pressure automatically drops and then re-builds the high pressure light will flash on and off until approximately 0.4 ml of anesthetic penetrates the ligament space to effect complete anesthesia of the tooth. If, however, the high pressure light remains lighted continuously, it means the flow is blocked by, for example, the lumen of the needle being pressed against a tooth surface in sealing relationship. There is no pressure-reducing flow through the ligament along the root of the tooth. The doctor can then remedy the blockage by simply turning or moving the needle.

In a significant percentage of PDL injections, however, the seal between ligament and the needle tip is not tight and the procedure will fail due to leakage. The present invention identifies the absence of leakage by providing an intermediate pressure sensor and indicator light. Leakage of the liquid, which is impossible to detect visually in the mouth, precludes pressure build-up and flow of anesthetic to the tooth nerves at the root. The intermediate pressure light will not illuminate. The doctor can then promptly move to remedy the problem by a variety of techniques including, for example, bearing down more firmly on the needle, tapping the back end of the needle handle, twisting the needle or even attempting a completely fresh seating of the needle tip in the ligament.

The methods and apparatus of the present invention also make possible a painless palatal injection by virtue of the ability to develop pressure identifiable by the pressure lights relatively quickly in a controlled manner within the palate sufficient to anesthetize both the ASA and MSA nerves from one injection site.

DESCRIPTION OF THE PREFERRED EMBODIMENTS

Figure 7:
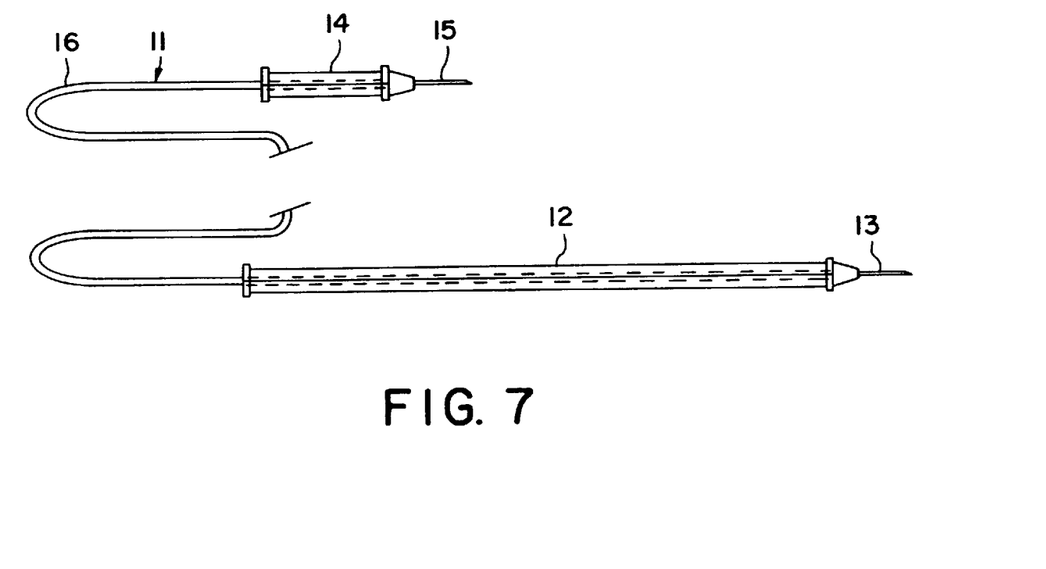
FIG. 7 is a side view of the disposable needle and conduit assembly in accordance with one embodiment of the invention.

Referring to FIGS. 1–5, one embodiment of the present invention is illustrated as embodied in an instrument 10 for injecting liquid local anesthetic from a disposable vial V into the tissues of a patient by means of a disposable needle and conduit assembly 11 having at one end a hand piece 12 carrying a hypodermic needle 13 and its other end a coupling member 14 carrying a hollow needle 15 which is adapted to penetrate the sealing membrane V-1 (FIG. 3) at the end of the conventional anesthetic vial V. The two ends of the assembly 11 are joined by flexible, micro-bore tubing 16. The assembly 11 and its structural details are more fully described below in reference to FIGS. 7, 8A, B, C and 9A, B and C.

The instrument 10 includes a reciprocatable yoke or carriage 17 which carries, detachably, the coupling member 14 of the needle and conduit assembly 11. The yoke 17 is movable, left and right as viewed in the drawing, between active and inactive positions to move the needle 15 into and out of the membrane of the vial V. The vial V is detachably mounted in a stationary yoke 18 in alignment with the needle 15. The yoke 17 is shifted by a hand knob 19 on the front of the instrument by means of a cam 20 shown in FIG. 3 (and also shown diagrammatically as a radius arm in FIG. 5). The yoke is carried by a stub shaft 21 slidably mounted in brackets 22 against a compression spring 23. A limit switch 24, hereafter called the priming switch, is engaged by the stub shaft 21 when the yoke is shifted to drive the needle 15 into the vial V to tap the contents.

The base end of the full vial V, which is sealed by a piston plug 25, is received in a sleeve 26 in alignment with a plunger 27 of a stepper motor 28. The stepper motor 28 drives the plunger back and forth via a conventional threaded coupling under the control of a microprocessor 29 which receives instructions from six control switches (including the priming switch 24). The switches are: a load vial switch 30 operated by the plunger 27 at its extreme left hand position as shown in the drawings; a patient-operated switch 31 which can be held by the patient and which can either be hard wired to the microprocessor or, in a preferred embodiment, connected by a conventional radio signal switch to avoid cumbersome wires; a doctor-operated foot switch 32 of the simple, single pole (off-on) variety; a first or intermediate pressure-responsive switch 33; and a second or high pressure-responsive switch 34. The circuit system is energized from the mains through a power switch 35 and a transformer T.

Indicator lights can be provided for the various switch functions such, for example, as light 35' indicating power, light 24' indicating the liquid system is primed, light 33' to indicate a first pressure in the liquid system, and light 31', 34' to indicate either a second pressure in the liquid system or a signal from the patient, or both. The lights are preferably differently colored to indicate their various signals to the doctor operating the instrument.

Figure 1:
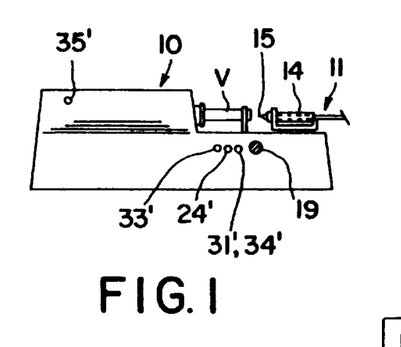
FIG. 1 is a partial, side view of an instrument for injecting local anesthetic.
Figure 2:
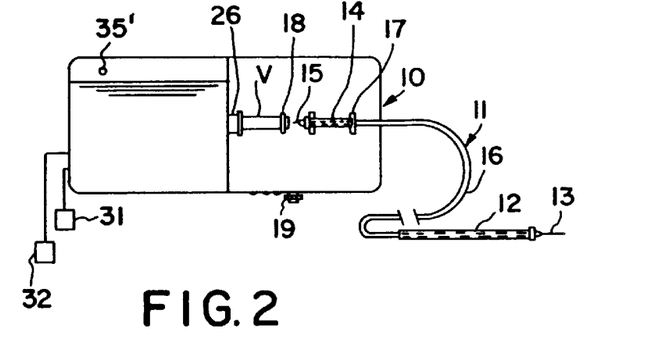
FIG. 2 is a top view of the instrument of FIG. 1.
Figure 3:
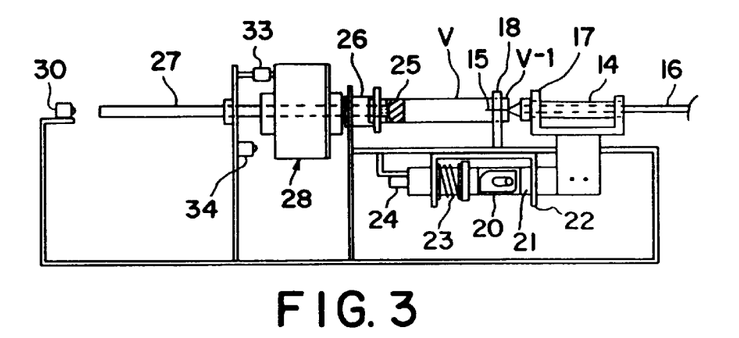
FIG. 3 is a partial, side view in enlarged scale of the internal mechanism of the instrument of FIGS. 1 and 2.
Figure 4:
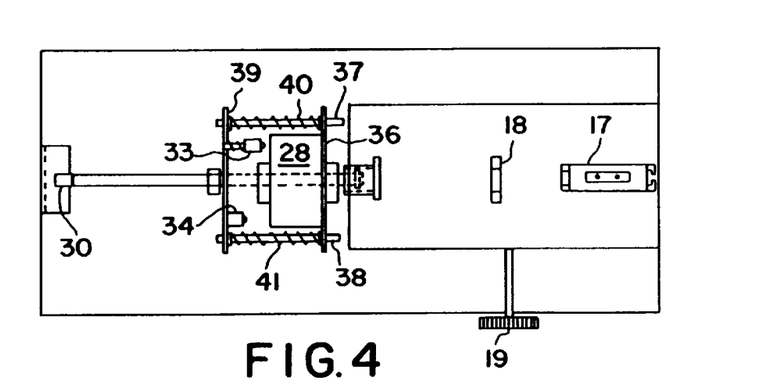
FIG. 4 is a top view of the mechanism of FIG. 3.
Figure 5:
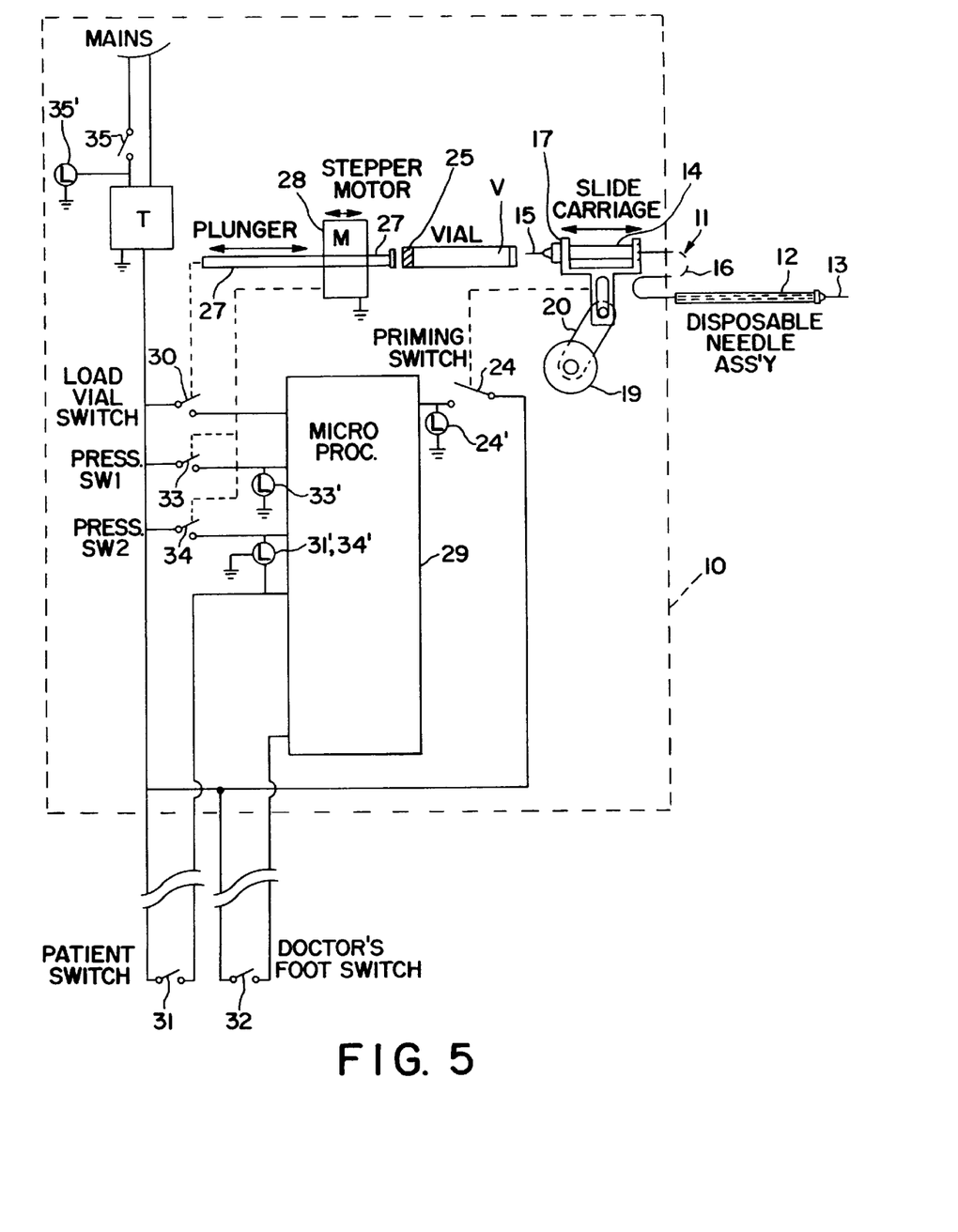
FIG. 5 is a schematic diagram of the circuitry and mechanism of the instrument.

An important feature of the invention is the means for sensing and controlling the liquid pressure in the system at the lumen or tip of the needle when it is embedded in the patient's tissue and discharging liquid anesthetic. The force against the piston 25 in the vial V by the plunger 27 is one preferred method of taking this measurement. To this end, the stepper motor 28 is slidably supported by a carrier plate 36 on two slide bars 37 and 38 (FIG. 4) secured to rigid frame piece 39. Pressure by the plunger 27 on the piston 25 of the vial V will work to push the motor backward i.e., to the left as viewed in the drawing. This backward movement is resisted by a pair of compression springs 40 and 41 surrounding the slide bars 37 and 38 and captured between the back of the motor 28 and the frame piece 39. The movement is measured by switches 33 and 34 which are differentially spaced from the motor as best seen in FIG. 3. The switch 33 is spring loaded to yield in translation after it is actuated to enable the switch to continue its movement to the second switch 34.

The intermediate pressure switch 33 is set to close when the force on the piston is approximately 7 to 12 pounds and the high pressure switch 34 when the pressure is approximately 27 pounds. So established, the apparatus is capable of performing, under the control of the microprocessor 29 as instructed by the six switches, the injection of local anesthetic into a patient.

In the illustrated embodiment of the invention, the screw pitch of the plunger 2 and the internal driving collar of the stepper motor 2 are selected so that for each step of rotation of the stepper motor the plunger moves 0.0005 inches. The microprocessor is programmed to step the motor at successively increasing rates to generate the flow rate curve of FIG. 6. In the first second 1 step is generated, in the second 4 steps are generated, in the third, there are 7 steps. The progression continues until the thirty-fifth second when the number of steps reaches 303, which as shown on the graph translates into plunger displacement of 0.1515 inches per second. This movement of the piston 25 of the vial V is generally recognized in medicine as the fastest rate of flow of anesthetic which should be administered to a patient. It will be seen, therefore, that for at least a substantial portion of the full injection period, e.g., 35 seconds in the illustrated embodiment, the flow rate curve preferably progressively steepens to the maximum flow rate and thereafter continues at a uniform maximum rate until the entire contents of the vial is injected into the patient. It will be understood, however, that many variations in the curve can be used within the scope of the invention provided, however, that a continuously increasing rate endures for a substantial fraction such as fifty to seventy-five percent of the duration of entire injection before the maximum rate is reached so that preliminary numbing always occurs before the maximum flow rate is reached. The use of a progressively steepening flow rate curve, as opposed for example, to a linear, continuously increasing flow rate, further assures that the amount of anesthetic injected at the beginning of the procedure is kept at a minimum to avoid premature build-up of pressure.

The procedure is begun with the plunger retracted to the position determined by activation of the "load vial" switch 30. The plunger 27 will be retracted sufficiently to allow the disposable vial V to be placed in its stationary holding yoke or carriage 18 with its base in the sleeve 26 aligned with the plunger 27. The yoke 18 secures the vial against axial movement. The disposable needle assembly 11 is then mounted by placing coupling portion 14 in the movable carrier yoke or carriage 17 which secures it against axial movement. The yoke 17 will have previously been positioned in its right hand position by the control knob 19. With the coupling portion secured, the knob is turned to drive the needle 15 through the sealing membrane V-1 of the vial V to enter the liquid reservoir and provide for the flow of liquid anesthetic through the flexible tube 16 and out of the needle 13. This priming function is provided automatically by the priming switch 24 which is activated by the stub shaft 21 which carries the traveling yoke 17. In response, the microprocessor 29 will index the stepper motor to advance the plunger 27 forward to enter the back end of the vial V and force the piston 25 a few millimeters into the vial to displace liquid therein to exhaust all air out of the disposable needle assembly.

The doctor next implants the needle in the patient's tissues to the medically dictated site which will enable liquid pumped through the needle 13 to reach the nerve site to be anesthetized. The step of implanting the needle into the tissue has now been determined not to be a significant source of discomfort or pain to patients, and, therefore, the prior art step of establishing liquid flow through the needle while implanting the needle is not necessary. Meantime, lights 35' and 24' will have indicated to the doctor that the system is primed and operative. The doctor next activates the foot switch 32 to start the flow of liquid anesthetic into the patient.

Figure 6:
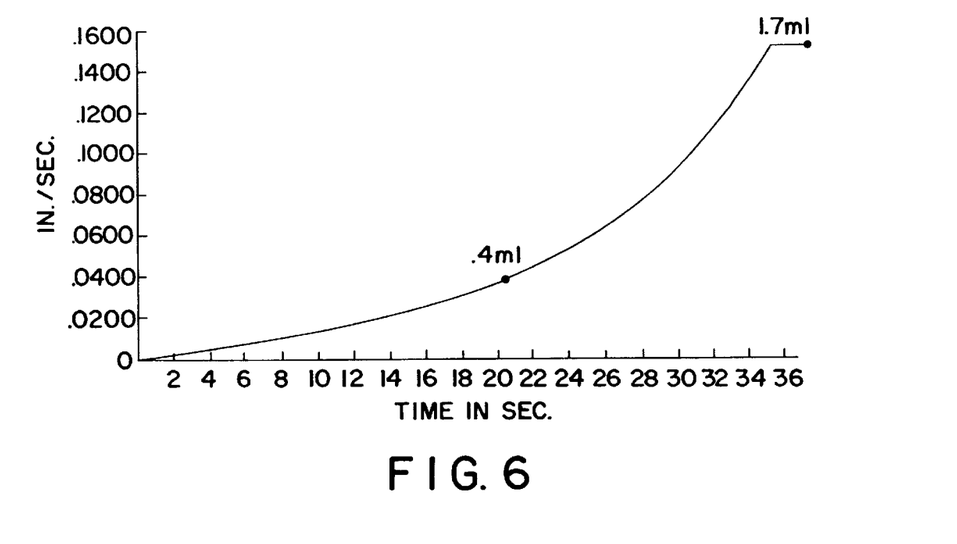
FIG. 6 is a graph of time versus anesthetic flow rate for the instrument.

Referring to FIG. 6, the microprocessor 29 will now instruct the stepper motor to advance the plunger 27 forward at ever increasing rates continuously to drive an ever increasing volume of anesthetic into the patient. The smoothed curve showing the increasing rate of plunger displacement is displayed by FIG. 6. At the 20 second interval on the x or time axis of the curve, approximately 0.4 ml, which is approximately a quarter of the contents of the vial, will have been delivered (in the absence of blockage of the flow which will be discussed below).

Figure 6A:
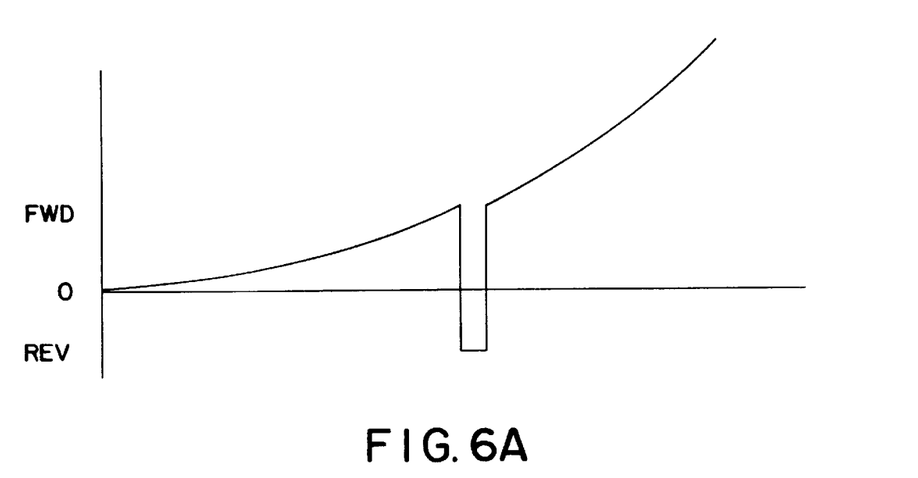
FIG. 6A and 6B are graphs corresponding to FIG. 6 showing, respectively, an aspiration cycle and patient's stop cycle.
Figure 6B:
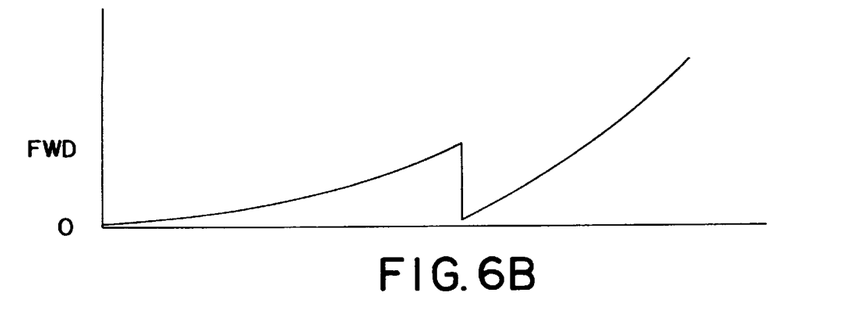

The doctor, by viewing the vial, can determine how much anesthetic has been delivered at any given time and will terminate the procedure by controlling the foot switch 32. Meantime, if the patient perceives discomfort, which is a precursor of pain, the patient switch 31 is actuated, signaling the microprocessor to reduce or stop the forward movement of the plunger, hence reducing the pressure (which is the source of the patient's discomfort). FIG. 6B shows modification of the plunger travel each time the patient senses the need for relief. The plunger travel then resumes, preferably but not necessarily, at the beginning rate, which is zero in the illustrated embodiment. The flow resumes, this time into partially anesthetized tissue. Several interruptions can occur in any given injection. Tests have established that one or two interruptions are the most that occur in the large majority of injections.

A full volume of liquid in the vial at the start of the actual infusion into the patient's tissue, or about 1.7 ml, will be infused after 36 seconds, assuming no interruptions. This corresponds to the clinically approved time for a full volume injection. Interruptions by the patient of course extend the time but the object of the invention is to perform the injection without pain to the patient. Thus the doctor does not have to impose his own judgement on the process which could in fact take longer than necessary for the comfort of the patient.

Certain injections require that the doctor determine that the flow of anesthetic is not being administered intravenously which occurs if the needle tip by chance comes to rest in a vein. To aspirate or reverse the flow (which will draw blood back into the hand piece 11 to be seen by the doctor), the doctor simply lifts his or her foot from the switch momentarily. This instructs the microprocessor to stop the forward movement of the plunger, reverse its movement for two seconds and then resume the forward movement. The doctor meantime will have reactivated the foot switch and the plunger rate of movement will resume at the rate at which it was interrupted, all as shown in FIG. 6A. While the vertical components of the curves of FIGS. 6A and 6B show theoretical instantaneous stopping and starting of the plunger 27 (FIG. 6B) and forward and reverse motion of the plunger (FIG. 6A) it will be understood that actual time motion curves would show at least some degree of time delay between the motion changes i.e. the vertical lines on the graph will be slightly inclined.

The invention provides means to enable the doctor to deliver the difficult but highly desirable intraligamentary or PDL injection in dentistry with success in the large majority of attempts. In the PDL injection, the doctor implants the needle firmly in the base of the sulcus to access the very narrow ligament space which separates the bone from the tooth. The resistance of the ligament space to the passage of liquid anesthetic varies widely, contributing to the difficulty of the injection, but when properly executed, the injection requires very little total volume of anesthetic, say 0.4 ml or one quarter of a full vial, and can be done rapidly and painlessly. Flow is started by actuating switch 32. If pressure does not build and the intermediate pressure switch 33 is not actuated, the doctor is informed that there is a free flow of anesthetic but not through the ligament. It may be flowing freely into the mouth or it may be flowing into soft tissue in dangerously large amounts. The doctor reacts promptly by more carefully or firmly implanting the needle until sufficient pressure is achieved to illuminate the intermediate pressure light 33'.

If, however, the pressure continues to build until the maximum pressure light 31', 34' illuminates continuously without flashing the doctor is informed that there may be complete blockage of flow caused, for example by the lumen of the needle being pressed against a tooth surface. This is a signal to the doctor to manipulate and/or twist the needle, or possibly to reimplant it, until the blockage is avoided and the flow of anesthetic is through the ligament space. If, however, light 33' is on and light 31', 34' is not, it is highly probable that the flow is through the ligament and the injection is a success. The doctor simply removes his foot from switch 32 when 0.4 ml has been infused and the procedure has been completed. If, however, the light 31', 34' cycles on and off (the light 33' also being lit) the doctor is told that anesthetic is working its way down the ligament space and that anesthesia will result when the appropriate amount has been administered. Overall, the doctor is given all the information necessary to effect successfully the difficult but highly useful and desirable PDL injection in the large majority of cases.

Referring to FIGS. 7, 8A, 8B, 8C, 9A, 9B and 9C, the structural and assembly detail of the disposable needle assembly 11 and its fluid tight coupling are shown in enlarged scale. The coupling member 14 at one end of the assembly and the hand-piece 12 at the other end are substantially identical, except for length, and only the latter will be described.

The hand-piece 12 is injection molded of plastic in two symmetrical, mirror-image, matable sections 12A and 12B. They can if desired be molded together with two clam shell hinges 40 joining them at both ends, as shown, or they can be separately molded. Each section includes an elongated tail piece 41 which is half-round on its external face and includes a half-round central groove 42 on its flat face and which serves as the handle when assembled. The two half-round grooves 42 are adapted to mate to define a central through-bore 42A (FIGS. 8C and 9A–C) to receive snuggly a short length of one end of the flexible micro-bore tube 16.

Figure 9A:
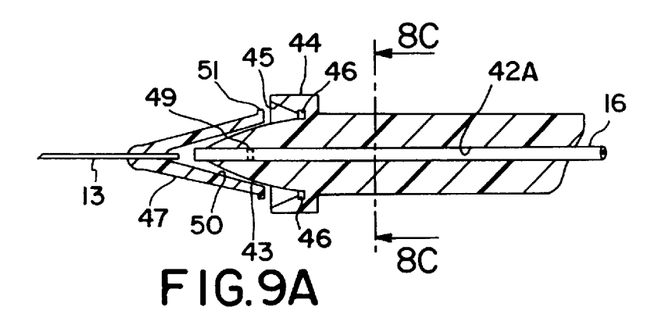
FIGS. 9A, 9B and 9C are views in enlarged scale and taken in longitudinal section showing the assembly detail of the disposable assembly shown in FIG. 7.
Figure 9B:
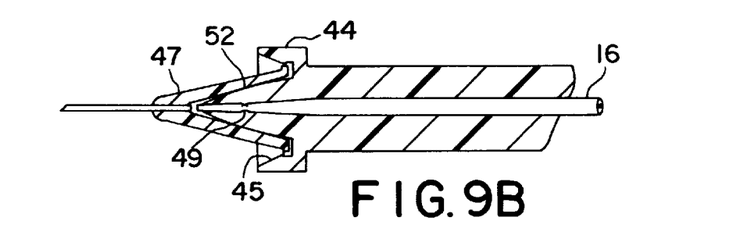
Figure 9C:
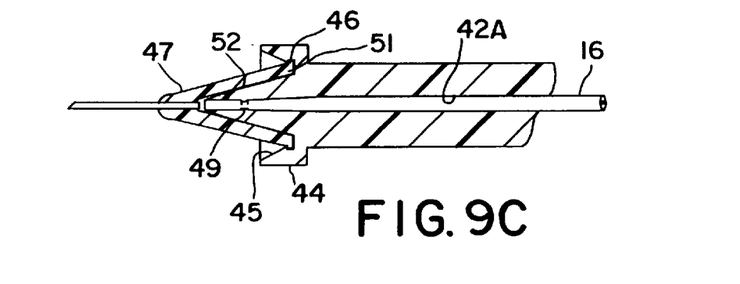

The forward end of each section 12A and 12B is gently rounded to form a convexly rounded, circular nose 43 when mated, as shown in FIGS. 9A, 9B and 9C to form a conical mating portion for the assembly. At the junction of the nose 43 and the tail piece 41 there is an integrally formed rib 44 having an inward taper 45 and an internal, circular groove 46 to receive a tip portion in the form of a conventional Luer Lock fitting 47 (FIGS. 9A–C) in which the base end of the needle 13 is sealed. Snap fittings 48A are formed on the section 12A to be received in apertures 48B in the section 12B to latch the hinged parts. Matched pairs of the snap fittings 48A and apertures 48B can be formed along the length of the tail piece, as required. At the back end of the hand piece a second rib 54 can be formed matching the forward rib 44 in radius to support the second clam shell hinge 40. The entire subassembly is preferably formed of resiliently compressible plastic material to perform the fluid tight sealing functions described below.

Figure 8A:
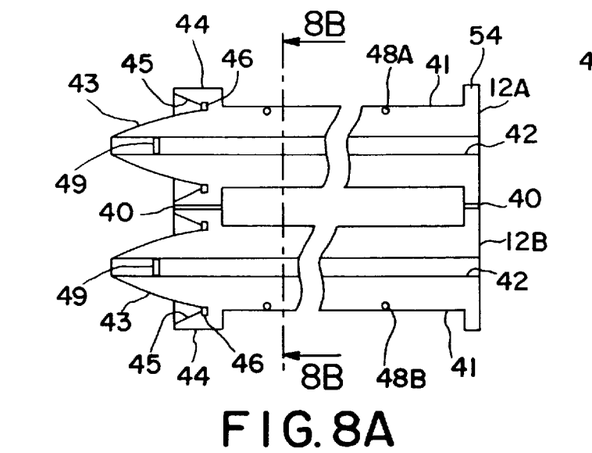
FIG. 8A is a plan view of the working end of the two-piece molding which when coupled forms an end unit of the disposable needle assembly of FIG. 7.
Figure 8B:
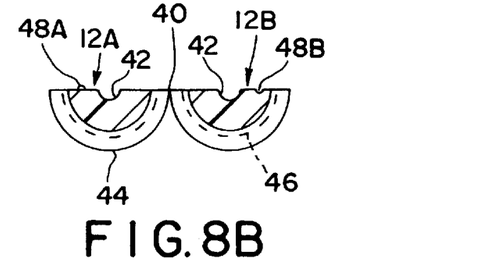
FIG. 8B is a view in cross-section taken on the line 8B—8B of FIG. 8A looking in the direction of the arrows.
Figure 8C:
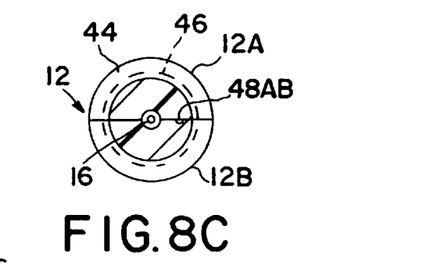
FIG. 8C is a view in cross-section taken on the line 8C—8C of FIG. 9A showing the two sections of FIG. 8A and FIG. 8B assembled.

In FIGS. 8C, 9A, 9B and 9C, the sections 12A and 12B are shown mated, with the micro-bore tube 16 captured in the groove 42A to reach the apex of the conical nose. As best seen in FIG. 8A, a shallow circumferential internal rib 49 is formed near each end of the grooves 42 to pinch the tube 16 in fluid tight sealing relationship. Referring to FIGS. 9A, 9B and 9C, the Luer Lock fitting 47 is shown, respectively, in its starting, intermediate and final positions receiving the nose 43 of the hand-piece. The fitting 47 includes an internal, conical space 50 to receive the convexly rounded nose 43, and an annular rib 51 to engage the inward taper 45 which cams the fitting radially inward in compression against the resilience inherent in the plastic materials. The internal conical space 50 of the Luer Lock fitting bears hard on a circular tangent line 52 on the nose 43 after the rib 51 has snapped into the internal groove 46 to complete and lock the assembly. Fluid tight pressure seals are established by the compression of the rib 49 embedded in the tube 16 and also at the circular tangent line 52 where the internal wall of the conical space 50 of the Luer Lock fitting 47 bears hard against the convexly rounded nose 43. The hand piece is, therefore, rendered liquid tight with respect to internal anesthetic pressure without requiring the use of solvents, sealing adhesives or the like. It will be observed that the tangent line 52 surrounds and is radially aligned with the bearing rib 49 which seals against the flexible micro bore conduit or tube 16. It will be understood that the convexly curved surface 43 and the rib 49 are functionally equivalent and the rib might also be formed as a more convexly rounded surface while the convexly rounded surface 43 might be formed as a more rib-like geometry. Also, the sealing rib or convexly rounded surface might also be formed on the internal conical surface 50 of the fitting 47. The coupling member or fitting 14 at the opposite end of the tube 46 is substantially identical but, there being no need for an elongated handle can be made substantially shorter in length to be received in the yoke 17 of the pumping apparatus 10.

What is claimed is:

1. Apparatus for the supervised administration of local anesthetic into the tissues of a patient through a hypodermic needle comprising;

a container comprising a local anesthetic injection solution for numbing a local area of the patient's body;

a hypodermic needle; and means for delivering said local anesthetic through the needle at a pre-programmed, gradually increasing rate of flow over a predetermined period of time representing at least a substantial portion of the entire time for the injection.

2. Apparatus according to claim 1, wherein said gradually increasing rate of flow is continuously increasing.

3. Apparatus according to claim 1, in which the flow rate curve progressively steepens with time.

4. Apparatus for the supervised administration of local anesthesia into tissues of a patient which are connected to the nerve sites to be blocked, said injection being through a hypodermic needle from which the local anesthesia is forced through the connecting tissue to the nerve site comprising:

a container comprising a local anesthesia injection solution for numbing a local area of the patient's body;

means for delivering the local anesthesia through the hypodermic needle into the connecting tissue at a pre-programmed rate of flow in which the rate increases with time and in which the time of rate increase is at least a substantial portion of the entire time for the injection.

5. Apparatus according to claim 4 in which the flow rate progressively steepens with time.

6. Apparatus according to claim 5 in which at least about 0.4 ml of local anesthesia is delivered in approximately 20 seconds.

7. Apparatus according to claim 6 in which at least about 1.7 ml of local anesthesia is delivered in approximately 36 seconds.

8. Apparatus according to claim 4 further comprising means for interrupting the flow and restarting the flow at a rate equal to or below the flow rate at the time of interruption.

9. Apparatus according to claim 8 further comprising means for reducing the anesthesia flow rate responsive to a pressure which is a function of the pressure of the anesthesia at the output of the needle.

10. Apparatus according to claim 8 further comprising means for reducing the anesthesia flow rate which is operated by the patient.

11. Apparatus according to claim 4 further comprising means for controlling the injection procedure operated by the medical supervisor comprising a single pole, single throw switch.

12. Apparatus according to claim 4 further comprising means for detecting and indicating to the supervisor the attainment of a predetermined pressure.

13. Apparatus according to claim 12 wherein said predetermined pressure is an intermediate pressure for the injection procedure.

14. Apparatus according to claim 12 wherein said predetermined pressure is a maximum pressure for the injection procedure.

* * * * *